(12) United States Patent
Noui-Mehidi et al.

(10) Patent No.: US 11,680,482 B2
(45) Date of Patent: Jun. 20, 2023

(54) IN-SITU THERMAL RESPONSE FLUID CHARACTERIZATION

(71) Applicant: Saudi Arabian Oil Company, Dhahran (SA)

(72) Inventors: Mohamed Nabil Noui-Mehidi, Dhahran (SA); Sameeh Issa Batarseh, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/984,844

(22) Filed: Aug. 4, 2020

(65) Prior Publication Data

US 2020/0362696 A1 Nov. 19, 2020

Related U.S. Application Data

(63) Continuation of application No. 15/710,288, filed on Sep. 20, 2017, now Pat. No. 10,738,602.

(51) Int. Cl.
  *E21B 49/08* (2006.01)
  *G01N 25/18* (2006.01)
  (Continued)

(52) U.S. Cl.
  CPC .............. *E21B 49/08* (2013.01); *E21B 47/07* (2020.05); *E21B 49/081* (2013.01); *G01N 25/18* (2013.01);
  (Continued)

(58) Field of Classification Search
  CPC . E21B 47/065; E21B 2049/085; G01N 25/18; G01N 33/2823
  See application file for complete search history.

(56) References Cited

U.S. PATENT DOCUMENTS

| 3,807,227 A | 4/1974 | Smith, Jr. |
|---|---|---|
| 3,981,187 A | 9/1976 | Howell |

(Continued)

FOREIGN PATENT DOCUMENTS

| WO | 2015137915 A1 | 9/2015 |
|---|---|---|
| WO | 2016161358 A1 | 10/2016 |

OTHER PUBLICATIONS

Boda, M.A., et al., "Analysis of Kinematic Viscosity for Liquids by Varying Temperature" International Journal of Innovative Research in Science, Engineering and Technology, vol. 4, Issue 4, Apr. 2015, pp. 1951-1954.

(Continued)

*Primary Examiner* — Jill E Culler
(74) *Attorney, Agent, or Firm* — Bracewell LLP; Constance G. Rhebergen; Brian H. Tompkins (57) ABSTRACT

Tools, processes, and systems for in-situ fluid characterization based on a thermal response of a fluid are provided. The thermal response of a downhole fluid may be measured using a downhole thermal response tool and compared with thermal responses associated with known fluids. The properties of the downhole fluid, such as heat capacity, diffusivity, and thermal conductivity, may be determined by matching the thermal response of the downhole fluid with a thermal response of a known fluid and using the properties associated with the known fluid. The composition of the downhole fluid may be determined by matching the viscosity of the downhole fluid to the viscosity of known fluid. A downhole thermal response tool for cased wellbores or wellbore sections and a downhole thermal response tool for openhole wellbores or wellbore sections are provided.

10 Claims, 6 Drawing Sheets

(51) Int. Cl.
*E21B 47/07* (2012.01)
*G01N 33/28* (2006.01)
*G01N 25/00* (2006.01)

(52) U.S. Cl.
CPC ........ *E21B 49/0875* (2020.05); *G01N 25/005* (2013.01); *G01N 33/2823* (2013.01)

(56) References Cited

U.S. PATENT DOCUMENTS

| | | |
|---|---|---|
| 4,343,181 A | 8/1982 | Poppendiek |
| 4,745,353 A | 5/1988 | Stewart et al. |
| 4,891,969 A | 1/1990 | Wayland et al. |
| 5,159,569 A | 10/1992 | Xu et al. |
| 6,343,507 B1 | 2/2002 | Felling et al. |
| 6,892,138 B2 | 5/2005 | Hashem et al. |
| 7,430,903 B2 | 10/2008 | Ramos |
| 7,717,172 B2 | 5/2010 | Sonne et al. |
| 8,360,635 B2 | 1/2013 | Huang et al. |
| 9,347,310 B2 | 5/2016 | Unalmis et al. |
| 9,513,272 B2 | 12/2016 | Larson |
| 2003/0145987 A1 | 8/2003 | Hashem |
| 2007/0119244 A1 | 5/2007 | Goodwin et al. |
| 2008/0083273 A1 | 4/2008 | Sroka et al. |
| 2010/0027581 A1 | 2/2010 | Sasaoka |
| 2015/0260662 A1 | 9/2015 | Edward et al. |
| 2016/0041142 A1 | 2/2016 | Freitas et al. |
| 2016/0258279 A1 | 9/2016 | Xia et al. |

OTHER PUBLICATIONS

International Search Report and Written Opinion for International Application No. PCT/US2018/051272 (SA5755) dated Feb. 1, 2019; pp. 1-15.

IN-SITU THERMAL RESPONSE FLUID CHARACTERIZATION

CROSS-REFERENCE TO RELATED APPLICATIONS

This application is a continuation of and claims priority from U.S. Non-provisional application Ser. No. 15/710,288 filed Sep. 20, 2017, and titled "IN-SITU THERMAL RESPONSE FLUID CHARACTERIZATION," a copy of which is incorporated by reference in its entirety for purposes of United States patent practice.

BACKGROUND

Field of the Disclosure

The present disclosure generally relates to analysis of fluids in hydrocarbon reservoirs. More specifically, embodiments of the disclosure relate to a downhole tool for the in-situ characterization of fluids in hydrocarbon reservoirs.

Description of the Related Art

Wells may be drilled into rocks to access fluids stored in geographic formations having hydrocarbons. Such a geographic formation may contain or be referred to as a "reservoir." Information about fluids in a hydrocarbon reservoir is important for properly characterizing the reservoir and conducting optimal drilling and production operations to efficiently extract hydrocarbons. Increasing the accuracy of this information may increase the accuracy of subsequent determinations used to characterize a reservoir. Various devices and techniques exist for determining the fluids information, such as downhole tools and core sampling of reservoir rock. These techniques have particular limitations and costs and may not provide the most accurate fluids information. For example, many devices and techniques are incapable of direct in-situ determination of fluids information. Moreover, the determination and inaccuracy of some fluids information may result in delays in drilling and production.

SUMMARY

Embodiments of the disclosure generally relate to the in-situ characterization of downhole fluids, such as oil, water, and oil-water mixtures, via a thermal response (for example, a cooling rate, heating rate, or both).

In one embodiment, a tool for determining the thermal response of a downhole fluid is provided. The tool includes a tool body defining a fluid inlet and an interior chamber configured to receive a fluid and a plurality of temperature sensors disposed at a respective plurality of positions along an axial length of the tool body. Each of the plurality of temperature sensors is configured to acquire a temperature measurement of the fluid and a heating element disposed at a position along the axial length of the tool body such that the heating element is disposed between two of the plurality of temperature sensors and the heating element is configured to heat the fluid. In some embodiments, the heating element is a ceramic mesh heating element coupled to a radiofrequency (RF) antenna. In some embodiments, each of the plurality of temperature sensors is a thermocouple. In some embodiments, each of the plurality of temperature sensors is an infrared sensor. In some embodiments, the heating element is a first heating element, the position is a first position, and the tool includes a second heating element disposed at a second position along the axial length of the tool body such that the heating element is disposed between a different two of the plurality of temperature sensors. The second heating element is configured to heat the fluid. In such embodiments, the first heating element is configured to heat to a first temperature and the second heating element is configured to heat to a second temperature.

In another embodiment, a tool for determining the thermal response of a downhole fluid. The tool includes a tool body and a plurality of temperature sensors disposed at a respective plurality of positions along an axial length of the tool body. Each of the plurality of temperature sensors configured to acquire a temperature measurement of a fluid external to the tool body. The tool further includes a heating element disposed at a position along the axial length of the tool body such that the heating element is disposed between two of the plurality of temperature sensors, the heating element configured to heat a region external to the tool body. In some embodiments, the heating element is a radiofrequency (RF) source coupled to a directional RF antenna. In some embodiments, the RF source is a rotational RF source rotatable around a circumference of the tool body. In some embodiments, each of the plurality of temperature sensors is a thermocouple. In some embodiments, each of the plurality of temperature sensors is an infrared sensor. In some embodiments, the heating element is a first heating element, the position is a first position, the region comprises a first region, and the tool includes a second heating element disposed at a second position along the axial length of the tool body such that the heating element is disposed between a different two of the plurality of temperature sensors. The second heating element is configured to heat the fluid. In such embodiments, the first heating element is configured to heat to a first temperature and the second heating element is configured to heat to a second region external to the tool body.

In another embodiment, a method of determining the properties of a fluid is provided that includes inserting a tool into a wellbore. The tool includes a tool body and a plurality of temperature sensors disposed at a respective plurality of positions along an axial length of the tool body. Each of the plurality of temperature sensors is configured to acquire a temperature measurement of the fluid. The method further includes receiving a respective plurality of temperature measurements from the plurality of temperature sensors of the tool, determining a thermal response of the fluid based on the plurality of temperature measurements, and determining at least one property of the fluid using the thermal response. In some embodiments, determining a property of the fluid using the thermal response includes matching the thermal response of the fluid to a thermal response of a known fluid and determining a property of the fluid from a property of the known fluid. In some embodiments, the at least one property includes at least one of a heat capacity, a diffusivity, and a thermal conductivity. In some embodiments, determining the thermal response of the fluid based on the plurality of temperature measurements includes plotting the plurality of temperature measurements versus time. In some embodiments, each of the plurality of temperature sensors is a thermocouple. In some embodiments, the tool body defines a fluid inlet and an interior chamber configured to receive the fluid. In such embodiments, the tool includes a heating element disposed at a position along the axial length of the tool body such that the heating element is disposed between two of the plurality of temperature sensors and is configured to heat the fluid. In such embodiments, the heating element is a first heating element, the position is a first position, and the tool includes a second heating element disposed at a second position along the axial length of the tool body such that the heating element is disposed between a different two of the plurality of temperature sensors. In such embodiments, the second heating element is configured to heat the fluid. In some embodiments, the tool includes a heating element disposed at a position along the axial length of the tool body such that the heating element is disposed between two of the plurality of temperature sensors. In such embodiments, the heating element configured to heat a region external to the tool body. In such embodiments, the heating element includes a first heating element, the position is a first position, the region comprises a first region, and the tool includes a second heating element disposed at a second position along the axial length of the tool body such that the heating element is disposed between a different two of the plurality of temperature sensors. In such embodiments, the second heating element is configured to heat the fluid. In some embodiments, the at least one property comprises viscosity and the method includes determining a composition of the fluid using the viscosity and at least one temperature of the plurality of temperature measurements. In some embodiments, determining a composition of the fluid using the viscosity and at least one temperature of the plurality of temperature measurements includes matching the viscosity of the fluid at the at least one temperature to the viscosity of a known fluid and determining a composition of the fluid from the composition of the known fluid.

In another embodiment, a system for determining the properties of a fluid in a wellbore is provided. The system includes a processor and a non-transitory computer-readable memory accessible by the processor and having executable code stored thereon. The executable code includes a set of instructions that causes the processor to perform operations include receiving a respective plurality of temperature measurements from the plurality of temperature sensors of a tool inserted in the wellbore, determining a thermal response of the fluid based on the plurality of temperature measurements, and determining at least one property of the fluid using the thermal response. In some embodiments, determining a property of the fluid using the thermal response includes matching the thermal response of the fluid to a thermal response of a known fluid; and determining a property of the fluid from a property of the known fluid. In some embodiments, the at least one property includes at least one of a heat capacity, a diffusivity, and a thermal conductivity. In some embodiments, determining the thermal response of the fluid based on the plurality of temperature measurements includes plotting the plurality of temperature measurements versus time. In some embodiments, the at least one property is viscosity and the operations include determining a composition of the fluid using the viscosity and at least one temperature of the plurality of temperature measurements. In some embodiments, determining a composition of the fluid using the viscosity and at least one temperature of the plurality of temperature measurements includes matching the viscosity of the fluid at the at least one temperature to the viscosity of a known fluid and determining a composition of the fluid from the composition of the known fluid.

DETAILED DESCRIPTION

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Figure 1:
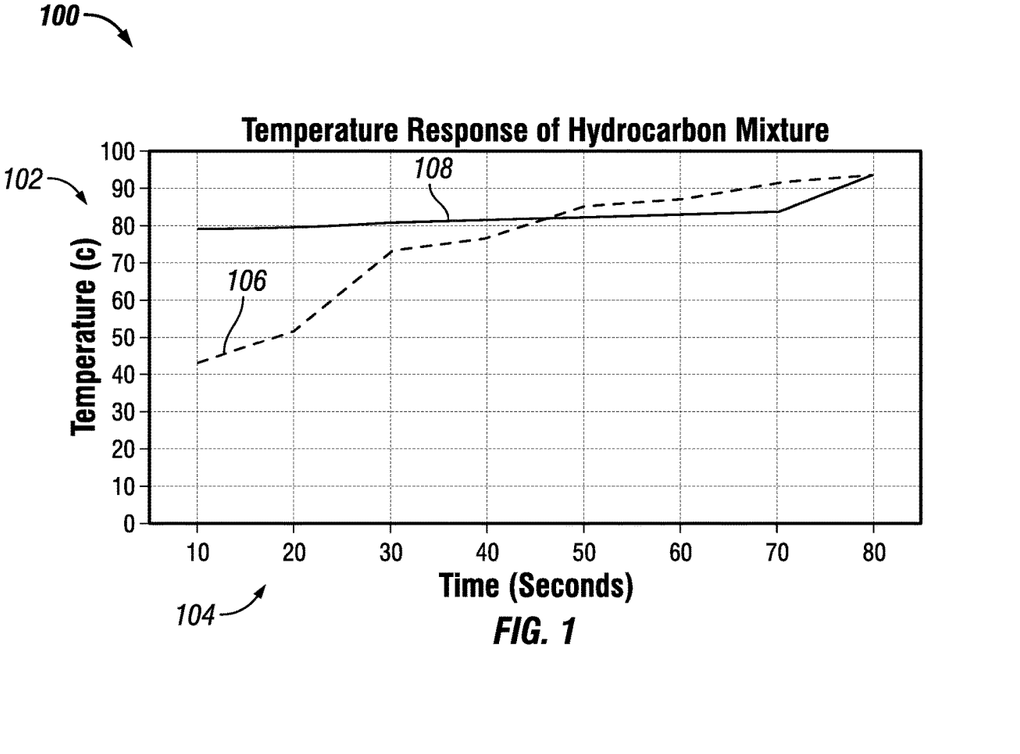
FIG. 1 depicts a graph of an example thermal response of an oil-water mixture of 10% oil and 90% water in accordance with an embodiment of the disclosure.

Downhole fluids, such as oil, water, and oil-water mixtures, may exhibit a thermal response (for example, a heating rate) when exposed to heat source, and may exhibit a thermal response (for example, a cooling rate) in the absence of the heat source. The thermal response may be a function of various thermal properties of the fluids, such as heat capacity, diffusivity, and thermal conductivity. The heating rate and cooling rate for a known fluid may be obtained from a database of fluid information or from analysis in a lab. For example, an oil-water mixture of 10% oil and 90% water exhibits a specific thermal response that may be shown as a thermal response curve. FIG. 1 depicts a graph 100 of an example thermal response of an oil-water mixture of 10% oil and 90% water in accordance with an embodiment of the disclosure. As shown in FIG. 1, the y-axis 102 depicts the temperature (in ° C.) and the x-axis 104 depicts the time (in seconds). The line 106 depicts the increase in temperature by heating the oil-water mixture with a heating source from 10 seconds to 80 seconds and recording the temperature every 10 seconds. The line 108 depicts the decrease in temperature from 80 seconds to 10 seconds after removing the heating source and recording the temperature every 10 seconds. As shown in FIG. 1, the oil-water mixture may exhibit specific thermal responses, such as when the fluid is heated as shown by line 106 and when the fluid is cooled as shown by line 108, that may be used to match unknown fluids having a similar thermal response.

With the foregoing in mind, embodiments of the disclosure are directed to tools, processes, and systems for in-situ fluid characterization based on a thermal response of a fluid. As discussed in the disclosure, the thermal response of a downhole fluid may be measured using a downhole thermal response tool. The thermal response may be compared with thermal responses associated with known fluids. The properties of a fluid, such as heat capacity, diffusivity, and thermal conductivity, may be determined by matching the thermal response of the downhole fluid with a thermal response of a known fluid and using the properties associated with the known fluid. In some embodiments, the viscosity of a fluid may be determined from the thermal response of the fluid. The composition of the fluid may then be determined using the viscosity and temperature measurements by matching the viscosity at a temperature to the viscosity of a known fluid having a known composition.

In some embodiments, a downhole thermal response tool for cased wellbores or cased wellbore sections may include a tool body that defines a fluid inlet and an interior chamber for receiving a fluid. The downhole thermal response tool may include temperature sensors disposed along an axial length of the tool body and one or more heating elements disposed at positions along the axial length of the tool body, such that a heating element is disposed between two temperature sensors. The heating elements may heat a fluid in the interior chamber of the downhole thermal response tool, and the temperature sensors may acquire temperature measurements of the fluid as it is heated and subsequently cools. The temperature measurements may be used to determine the thermal response of the downhole fluid. The thermal response may be compared to the thermal responses of known fluids to identify properties of the fluid, as discussed in the disclosure.

In some embodiments, a downhole thermal response tool for openhole wellbores or openhole wellbore sections may include a tool body having temperature sensors disposed along an axial length of the tool body and one or more heating elements disposed at positions along the axial length of the tool body that are configured to heat a surrounding formation. The heating elements may heat a fluid in the formation surrounding the downhole thermal response tool, and the temperature sensors may acquire temperature measurements of the surrounding fluid as it is heated and subsequently cools. The temperature measurements may be used to determine the thermal response of the downhole fluid, and the thermal response may be compared to the thermal responses of known fluids to identify properties of the fluid.

Figure 2:
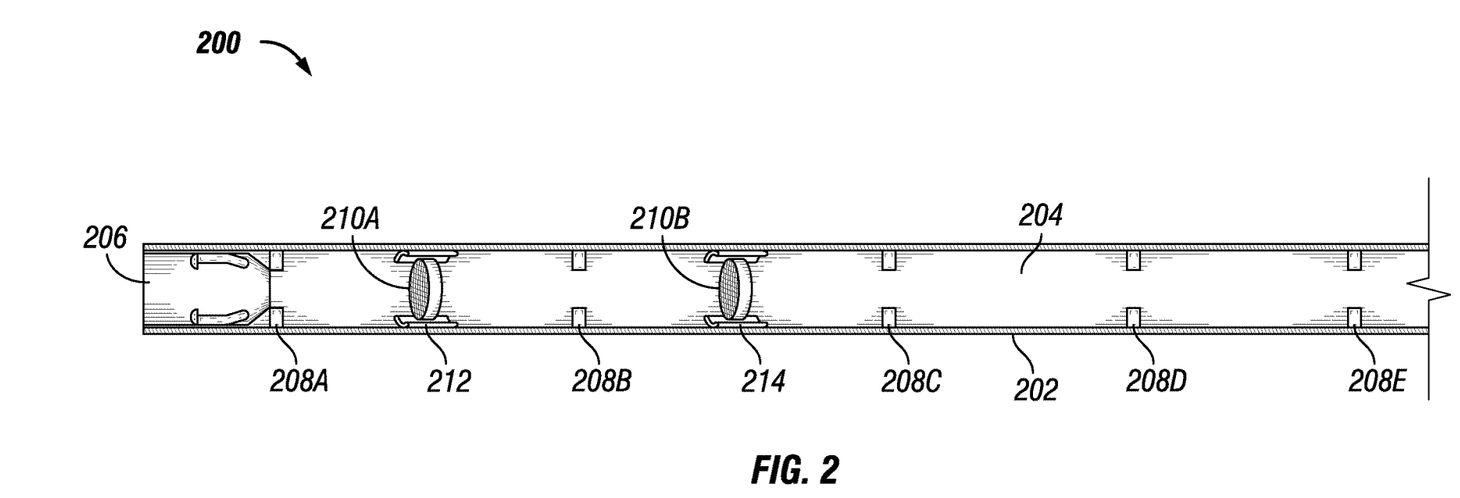
FIG. 2 is a schematic diagram of a downhole thermal response tool for determining the in-situ thermal response of a fluid in accordance with an embodiment the disclosure.

FIG. 2 is a schematic diagram of a downhole thermal response tool 200 for determining the in-situ thermal response of a fluid and corresponding fluid properties in accordance with an embodiment the disclosure. The downhole thermal response tool 200 includes a tool body 202 defining an interior chamber 204 and a fluid inlet 206. The downhole thermal response tool 200 may include one or more temperature sensors 208 and one or more heating elements 210. Each of the heating elements 210 may be coupled to a radiofrequency (RF) antenna 212.

The temperature sensors 208 may be positioned to measure the temperature of a fluid flowing through the interior chamber 204 of the tool 200. In some embodiments, each of the temperature sensors 208 may be a thermocouple or an infrared (IR) sensor. In some embodiments, the temperature sensors 208 may be a combination of thermocouples and IR sensors. In other embodiments, the temperature sensors may include other suitable types of temperature sensors. As will be appreciated, each of the temperature sensors 208 may be fiber optic and may, in some embodiments, be a circular sensor disposed around an inner circumference of the tool body 202.

The heating elements 210 may be positioned to heat the temperature of a fluid flowing through the interior chamber 204 of the tool 200. In some embodiments, each heating element 210 may heat to a different temperature. For example, in such embodiments, the heating element 210A may heat to a first temperature and the heating element 210B may heat to second temperature. The heating elements 210 may each be a filament or other heating element. In some embodiments, the heating elements 210 may each be a ceramic mesh heating element activated by radiofrequency (RF) antennas 212. In some embodiments, for example, such a ceramic mesh heating element may be activated by one of the corresponding radiofrequency (RF) antennas 212 before using the tool 200 to determine the thermal response of a fluid. The ceramic mesh heating elements may be activated before using the tool to provide a heating time period sufficient for the ceramic mesh heating elements to reach a specific temperature. By way of example, some embodiments of a ceramic mesh heating element may reach a specific temperature in a heating time period of about 3 minutes.

The temperature sensors 208 and heating elements 210 may work in combination to determine the thermal response of a fluid flowing through the interior chamber 202 of the tool 200. An example operation of the temperature sensors 208 and heating elements 210 is described infra. However, it should be appreciated that other embodiments of the tool 200 may include different numbers of temperature sensors and heating elements that operate in a manner similar to that described in the disclosure.

In the embodiment shown in FIG. 2, a fluid may enter the interior chamber 204 via the fluid inlet 202, as shown by arrow 214. An initial temperature of the fluid may be measured by temperature sensor 208A. The fluid may subsequently be heated by heating element 210A activated by RF antenna 212A, and the increased temperature of the heated fluid may be measured by temperature sensor 208B. In the embodiment shown in FIG. 2, the fluid may be subsequently heated by ceramic heating element 210B activated by RF antenna 212B, and the increased temperature of the heated fluid may be measured by temperature sensor 208C. Next, the additional temperature sensors 208 located downstream of the temperature sensor 208C may measure decreased in temperature of the fluid as the fluid cools while flowing through the interior chamber 204. For example, temperature sensors 208 D and 208E may measure the temperature of the fluid as it flows through the interior chamber 204 to exit the tool via a fluid outlet 216. In this manner, a temperature profile of the fluid flowing through the tool 200 may be determined.

In other embodiments, a tool may have more or less heating elements and temperature sensors. For example, although the tool 200 shown in FIG. 2 includes two pairs of a heating element and downstream temperature sensor, other embodiments of the tool may include three pairs of a heating element and downstream temperature sensor, four pairs of a heating element and downstream temperature sensor, five pairs of a heating element and downstream temperature sensor, or greater than five pairs of a heating element and downstream temperature sensor. In some embodiments, the tool may include more than one temperature sensor downstream of the ceramic heating element and upstream of the next ceramic heating element. In some embodiments, the tool 200 may include more than two temperature sensors after a heating element and downstream temperature sensor pair and before the fluid outlet of the tool 200.

Figure 3:
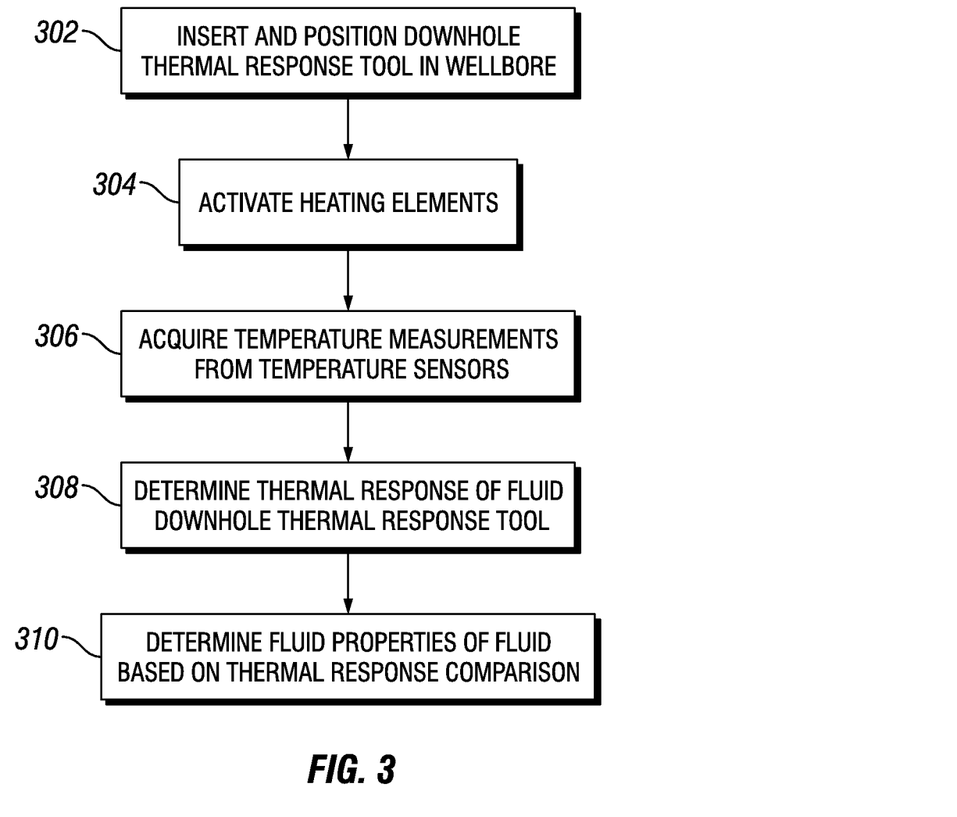
FIG. 3 is a flowchart of a process for determining the fluid properties of a downhole fluid using a downhole thermal response tool in accordance with an embodiment the disclosure.

FIG. 3 depicts a process of operation of the tool 200 in accordance with an embodiment of the disclosure. Initially, the tool 200 may be inserted in a wellbore and positioned at an appropriate distance within the wellbore suitable for measuring a fluid of interest (block 302). Next, the heating elements of the tool 200 may be activated to heat to a desired temperature (block 304). After the heating elements have reached a desired temperature, the temperature measurements of the fluid flowing through the tool 200 may be acquired using the temperature sensors (block 306). In some embodiments, the temperature measurements may be acquired over a duration. In some embodiments, a single set of temperature measurements may be acquired over the duration. For example, the initial temperature measurement may be acquired at time (t)=0, and the additional temperature measurements may be acquired at t+n, wherein n is an amount of time. For example, if n=2 seconds, the initial temperature measurement may be acquired at t=0, the temperature measurement from the second temperature sensor may be acquired at 2 seconds, the temperature measurement from the third temperature sensor may be acquired at 3 seconds, the temperature measurement from the fourth temperature sensor may be acquired at 4 seconds, and so on. In some embodiments, multiple sets (for example, multiple temperature measurements from each temperature sensor or multiple temperature measurements from one or more temperature sensors) may be acquired over the duration.

After acquiring the temperature measurements of the fluid flowing through the tool 200, the thermal response of the fluid may be determined (block 308). In some embodiments, for example, the temperature measurements may be transmitted to the surface over a connection, and the thermal response may be determined at the surface by a thermal response determination system. After determination of the thermal response, the thermal response of the downhole fluid may be compared to a database of thermal responses, and a match may be determined. As will be appreciated, the match may be determined using known techniques for curve matching. After matching the thermal response of the downhole fluid to a thermal response of a known fluid, the fluid properties of the downhole may be determined from the thermal properties of the known fluid (block 310).

Figure 4:
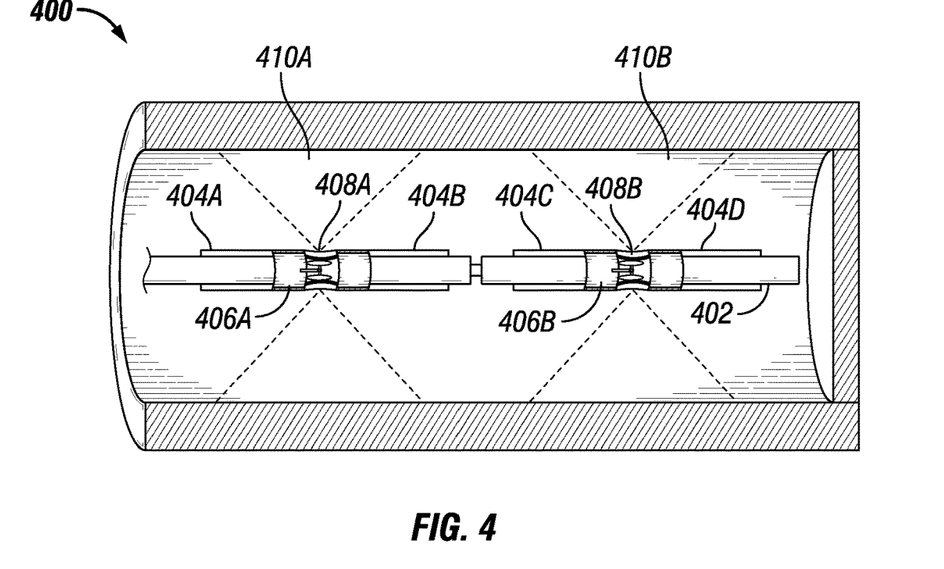
FIG. 4 is a schematic diagram of a downhole thermal response tool for determining the in-situ thermal response of a fluid in an openhole well in accordance with an embodiment the disclosure.

FIG. 4 is a schematic diagram of a downhole thermal response tool 400 for determining the in-situ thermal response of a fluid and corresponding fluid properties in an openhole well in accordance with an embodiment the disclosure. The downhole thermal response tool 400 includes a tool body 402, one or more temperature sensors 404 and one or more heating elements (for example, RF sources 406). Each of the RF sources 406 may be coupled to a radiofrequency (RF) antenna 408. In contrast to the tool 200 shown in FIG. 2 and described supra, the downhole thermal response tool 400 does not include an interior chamber that receives a fluid for flowing through the tool. As described infra, the downhole thermal response tool 400 directs heat into a surrounding formation to heat a surrounding fluid and then measure the temperature of the fluid.

The temperature sensors 404 may be positioned to measure the temperature of a fluid surrounding. In some embodiments, each of the temperature sensors 404 may be a thermocouple or an infrared (IR) sensor. In some embodiments, the temperature sensors 404 may be a combination of thermocouples and IR sensors. In other embodiments, the temperature sensors may include other suitable types of temperature sensors. As will be appreciated, each of the temperature sensors 404 may be fiber optic and may, in some embodiments, be a circular sensor disposed around an outer circumference of the tool body 402.

As shown in FIG. 4, the RF sources 406 and associated RF antennas 408 may be positioned to direct heat to a respective target zones and heat a fluid surrounding the tool body 402. In some embodiments, the RF sources 406 may each positioned internally within the tool body 402. The RF sources 406 may be activated to generate energy directed to the target zones 410 via the directional antennas 408. The directional antennas 408 may any suitable directional antenna that provides a specific voluminous coverage of the target zones 410. In some embodiments, the directional antennas 408 may each be a circumferential antenna that is disposed around a 360° circumference of the tool body 402 at a specific location along the length of the tool body 402.

In some embodiments, for example, the RF sources 406 may be activated to provide a heating time period sufficient for the target zones 410 to reach a specific temperatures. In some embodiments, each RF source 406 may heat to a different temperature. For example, in such embodiments, the RF source 406A may heat to a first temperature and the RF source 406B may heat to second temperature.

In some embodiments, the RF sources 406 may each be a rotatable RF source that is rotatable around the circumference of the tool body 402. In such embodiments, each rotatable RF source may be an electrically or hydraulically rotatable RF source such as known in the art. For example, in some embodiments, each RF source 406 may be coupled to an electric motor that rotates an associated RF source in response to a control signal transmitted to the tool 400. As shown in FIG. 4 for example, the RF source 406A may be rotated to correspondingly rotate the target zone 410A around the circumference of the tool body 402. In such embodiments, an RF source may be used to heat a target zone and temperature measurements may be acquired after a fluid in the target zone is heated. After heating, the RF source may be rotated around the circumference (for example, 360°) of the tool body 402, additional temperature measurements may be acquired as the previously heated fluid in the target zone cools. In some embodiments, the speed of the rotation of the RF source may be controlled to control (for example, increase or decrease) the time for the RF source to rotate around the circumference of the tool body 402. In this manner, multiple temperature measurements of a heated and cooled fluid in a target zone may be obtained.

The temperature sensors 404, the RF sources 406 and associated RF antennas 408 may work in combination to determine the thermal response of a fluid surrounding the tool body 402 of the tool 400. An example operation of the temperature sensors 404, the RF sources 406 and associated RF antennas 408 is described infra. However, it should be appreciated that other embodiments of the tool 400 may include different numbers of temperature sensors and heating elements that operate in a manner similar to that described in the disclosure.

After positioning the tool 400 in an openhole wellbore, an initial temperature of a surrounding fluid may be measured by temperature sensor 404A. The surrounding fluid in the target zone 410A may be heated by RF source 406A and directional antenna 408A. The increased temperature of the heated fluid may be measured by temperature sensor 404B. In the embodiment shown in FIG. 4, a second initial temperature of a surrounding fluid may be measured by temperature sensor 404C. The surrounding fluid in the target zone 410B may be heated by RF source 406B and directional antenna 408B. The increased temperature of the heated fluid may be measured by temperature sensor 406D. In this manner, a temperature profile of fluid surrounding the tool 402 may be determined.

In other embodiments, the tool 400 may have more RF heating components and temperature sensors. For example, although the tool 400 shown in FIG. 2 includes two sets of a RF heating components and temperature sensor, other embodiments of the tool may include three sets of a RF heating components and temperature sensor, four sets of a RF heating components and temperature sensor, five sets of a RF heating components and temperature sensor, or greater than five sets of a RF heating components and temperature sensor.

Figure 5:
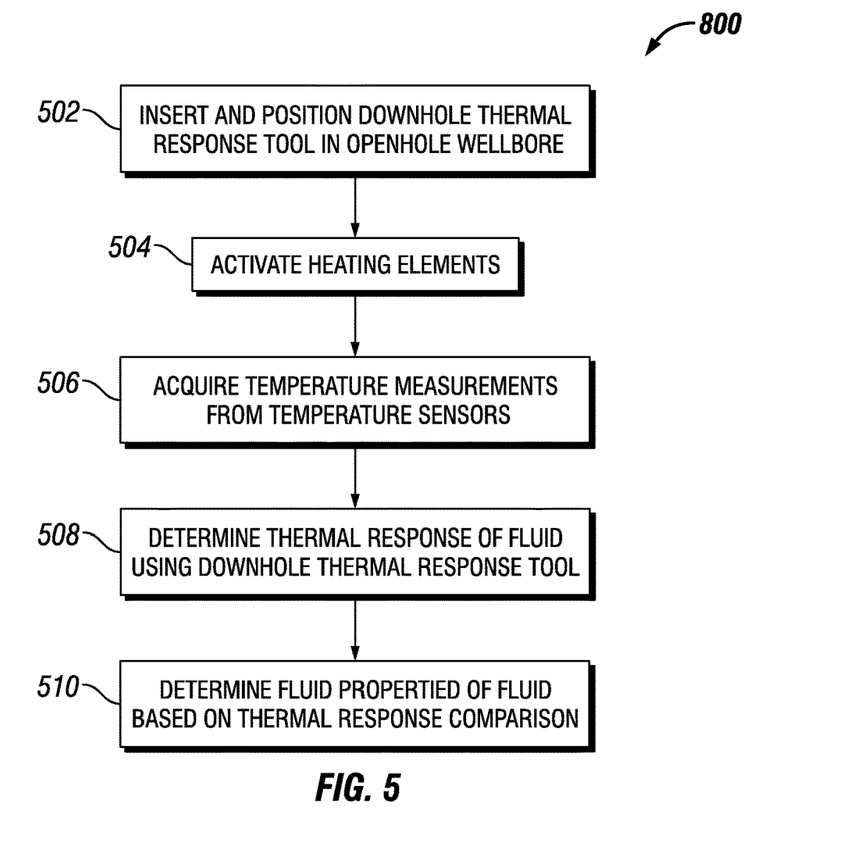
FIG. 5 is a flowchart of a process for determining the fluid properties of a downhole fluid using a downhole thermal response tool in accordance with an embodiment the disclosure.

FIG. 5 depicts a process of operation of the tool 400 in accordance with an embodiment of the disclosure. Initially, the tool 400 may be inserted in an openhole wellbore and positioned at an appropriate distance within the wellbore suitable for measuring a fluid of interest (block 502). In some embodiments, the tool 400 may include a number of heating elements and temperature sensors sufficient to measure a single zone in the openhole wellbore, multiple zones in the openhole wellbore, or the entire wellbore.

Next, the heating elements of the tool 400 may be activated to heat to a desired temperature and subsequently heat the surrounding formation and fluid (block 504). After the heating elements have reached a desired temperature, the temperature measurements of the fluid surrounding the tool 400 may be acquired using the temperature sensors (block 506). In some embodiments, the temperature measurements may be acquired over a duration. In some embodiments, a single set of temperature measurements may be acquired over the duration. For example, the initial temperature measurement may be acquired at time (t)=0, and the additional temperature measurements may be acquired at t+n, wherein n is an amount of time. For example, if n=2 seconds, the initial temperature measurement may be acquired at t=0, the temperature measurement from the second temperature sensor may be acquired at 2 seconds, the temperature measurement from the third temperature sensor may be acquired at 3 seconds, the temperature measurement from the fourth temperature sensor may be acquired at 4 seconds, and so on. In some embodiments, multiple sets (for example, multiple temperature measurements from each temperature sensor or multiple temperature measurements from one or more temperature sensors) may be acquired over the duration.

After acquiring the temperature measurements of the fluid surrounding the tool 400, the thermal response of the fluid may be determined (block 508). In some embodiments, for example, the temperature measurements may be transmitted to the surface over a connection, and the thermal response may be determined at the surface by a thermal response determination system. After determination of the thermal response, the thermal response of the downhole fluid may be compared to a database of thermal responses, and a match may be determined. As will be appreciated, the match may be determined using known techniques for curve matching. After matching the thermal response of the downhole fluid to a thermal response of a known fluid, the fluid properties of the downhole may be determined from the thermal properties of the known fluid (block 510).

Figure 6:
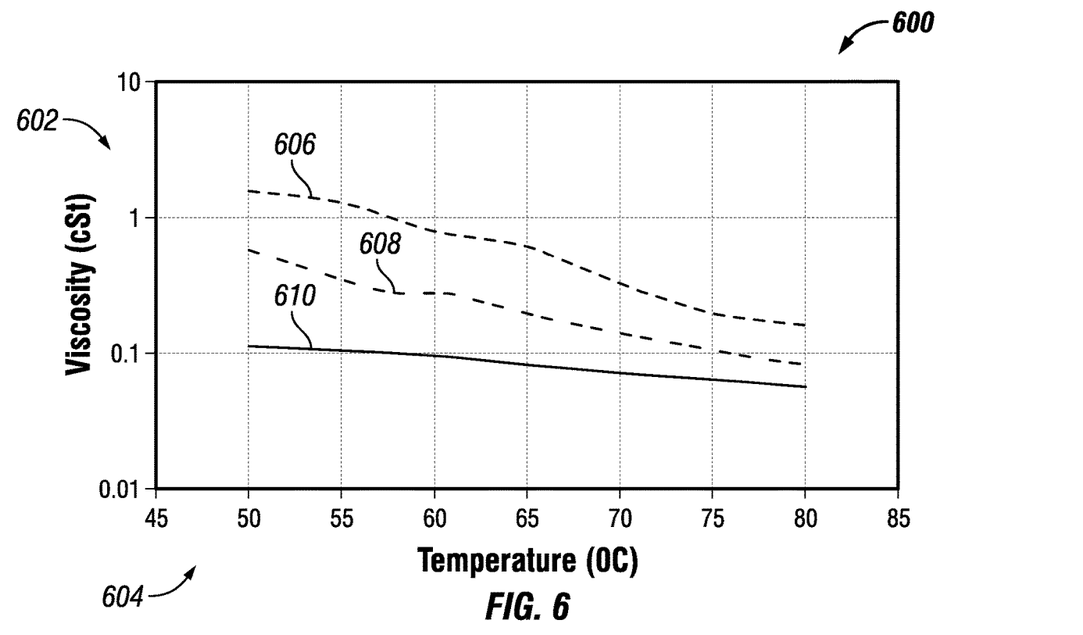
FIG. 6 depicts a graph of viscosity vs. temperature behavior for engine oil, water, and a water-oil mixture in accordance with an embodiment of the disclosure.

In additional embodiments, a downhole thermal response tool may be used to determine the viscosity and, from the viscosity the composition, of a downhole fluid. FIG. 6 depicts a graph 600 of the viscosity vs. temperature behavior for engine oil, water, and a water-oil mixture in accordance with an embodiment of the disclosure. As shown in FIG. 6, the y-axis 102 depicts the viscosity (in centistokes (cSt)) and the x-axis 604 depicts the temperature (in ° C.). As shown in FIG. 6, line 106 depicts the viscosity vs. temperature behavior for an engine oil, line 108 depicts the viscosity vs. temperature behavior for an engine oil, and line 110 depicts the viscosity vs. temperature behavior for water. For each temperature, each composition shown in the graph 600 has a viscosity determined along the respective viscosity vs. temperature line. For example, at a temperature of 60° C., the line 110 indicates that water has a viscosity of about 0.1 cSt, and the line 106 indicates that the water-oil mixture has a viscosity of about 0.5 cSt.

Figure 7:
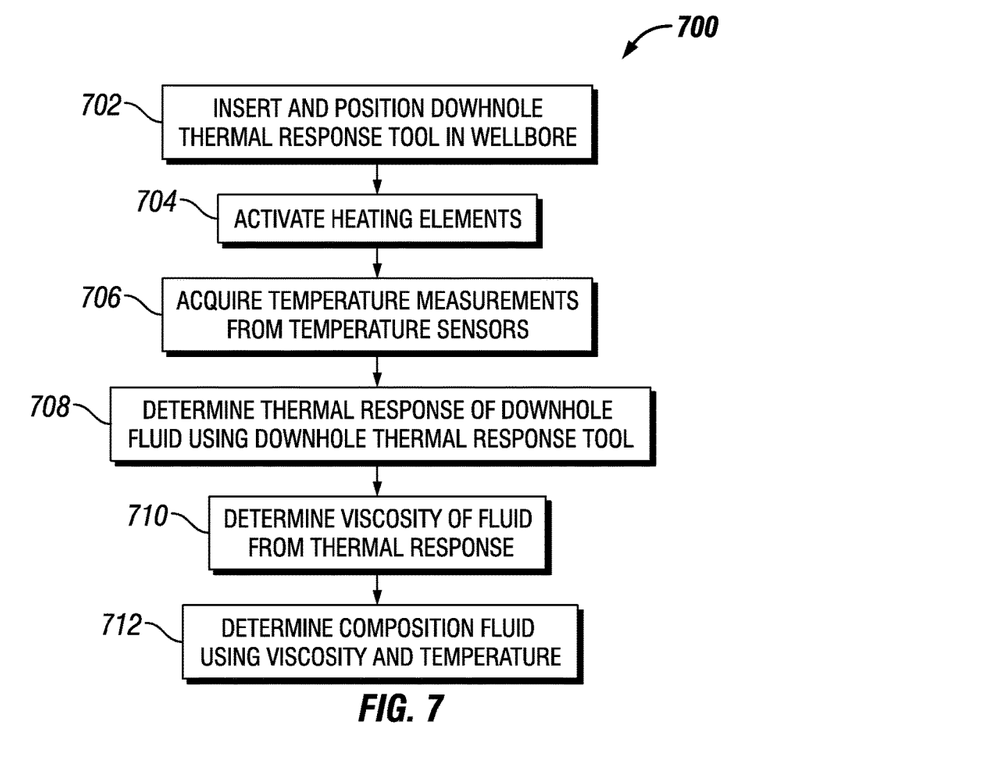
FIG. 7 is a flowchart of a process for determining the composition of a downhole fluid using a downhole thermal response tool in accordance with an embodiment the disclosure.

Accordingly, in some embodiments the thermal response of downhole fluid obtained using the downhole thermal response tool described in the disclosure may be used to determine the viscosity of the downhole fluid. Using the viscosity, the composition of the downhole fluid may be determined. FIG. 7 depicts a process 700 for determining the composition of a downhole fluid using a downhole thermal response tool in accordance with an embodiment of the disclosure. Initially, the tool 700 may be inserted in a wellbore (for example, a cased wellbore or an openhole wellbore using the appreciate embodiment of the downhole thermal response tool) and positioned at an appropriate distance within the wellbore suitable for measuring a downhole fluid of interest (block 702).

Next, the heating elements of the tool may be activated to heat to a desired temperature (block 704). After the heating elements have reached a desired temperature, the temperature measurements of the downhole fluid (for example, the fluid in the tool body in a cased wellbore or surrounding the tool body in an open hole wellbore) may be acquired using the temperature sensors (block 708). In some embodiments, the temperature measurements may be acquired over a duration. In some embodiments, a single set of temperature measurements may be acquired over the duration. For example, the initial temperature measurement may be acquired at time (t)=0, and the additional temperature measurements may be acquired at t+n, wherein n is an amount of time. For example, if n=2 seconds, the initial temperature measurement may be acquired at t=0, the temperature measurement from the second temperature sensor may be acquired at 2 seconds, the temperature measurement from the third temperature sensor may be acquired at 3 seconds, the temperature measurement from the fourth temperature sensor may be acquired at 4 seconds, and so on. In some embodiments, multiple sets (for example, multiple temperature measurements from each temperature sensor or multiple temperature measurements from one or more temperature sensors) may be acquired over the duration.

After acquiring the temperature measurements, the thermal response of the fluid may be determined (block 708). In some embodiments, for example, the temperature measurements may be transmitted to the surface over a connection, and the thermal response may be determined at the surface by a thermal response determination system. After determination of the thermal response, the viscosity of the downhole fluid may be determined using known correlations between the time and temperature of the thermal response and viscosity (block 710). In some embodiments, correlations may be determined in via laboratory analysis of fluids by measuring the viscosity when measuring the thermal responses of fluids. For example, viscosity may be determined from a heating time at a temperature and a cooling time at a temperature. The viscosity at a temperature within the measured thermal response may then be used to determine the composition of the downhole fluid by comparison to viscosities of known fluids at the same temperature (block 712). For example, as shown in FIG. 6, a viscosity at a particular temperature (for example, the temperature of a heating element in the downhole thermal response tool) may be indicative of the composition of a fluid. The viscosity at a particular temperature may be matched to a viscosity of a known fluid at the same temperature. For example, the viscosity of the downhole fluid may be compared to a database of viscosities, and a match may be determined. In this manner, a downhole fluid may be identified as oil, water, an oil-water mixture of a particular ratio, etc.

Figure 8:
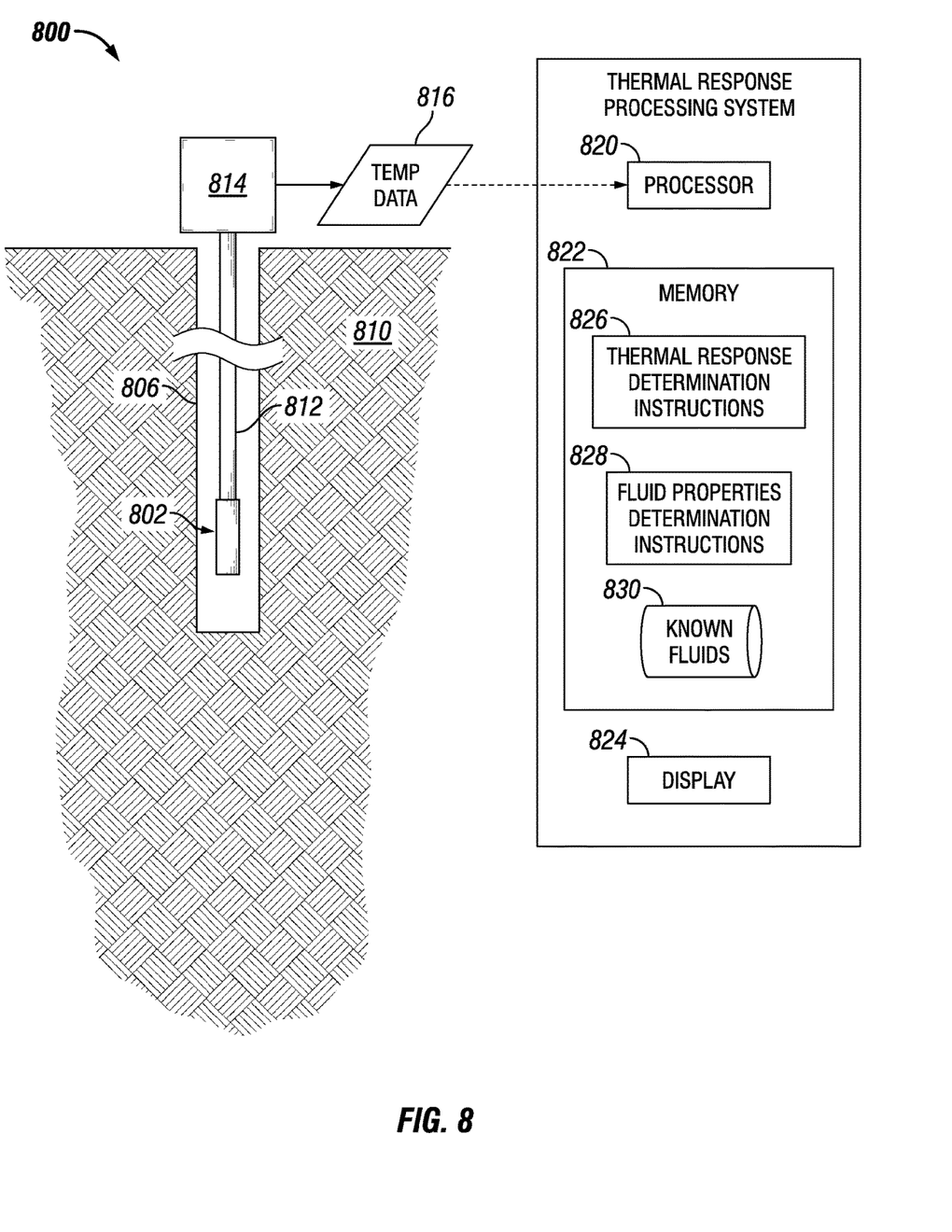
FIG. 8 is a schematic diagram of a well site having a downhole thermal response tool and a thermal response processing system in accordance with an embodiment of the disclosure.

FIG. 8 depicts a well site 800 that includes a downhole thermal response tool 802 for determining a thermal response of a downhole fluid and a thermal response processing system 804 in accordance with an embodiment of the disclosure. In the illustrated embodiment, the downhole thermal response tool 802 is inserted in well 804 defining a wellbore 806 extending into a formation 810. The wellbore 806 may be, for example, the wellbore 806 of any suitable type of well, such as exploration well, a crestal well, or other types of wells drilled to explore a reservoir.

As will be appreciated, FIG. 8 depicts a well site 800 that may include a cased wellbore or an openhole well. That is, the wellbore 806 shown in FIG. 8 may represent a cased wellbore or an openhole wellbore. Accordingly, the downhole thermal response tool 802 may include embodiments such as the downhole thermal response tool 200 described supra and suitable for use in a cased wellbore or the downhole thermal response tool 400 described supra and suitable for use in an openhole wellbore.

The wellbore 806 may include any form of a hole formed in a geologic formation, such as for the purpose of locating and extracting hydrocarbons or other resources from the formation 810. For example, the formation 810 may include an oil and gas reservoir, and the wellbore 806 may include a wellbore drilled into the formation 810 for the purpose of locating and obtaining information about the oil, gas and other hydrocarbons in the reservoir.

In some embodiments, the downhole thermal response tool 802 may be a wireline tool suspended on a wireline 812. The wireline 812 may include a conductor and may enable data transmission between the wireline tool 802 and a wireline monitoring and control system 814. For example, control signals may be transmitted to the wireline tool 802 to control operation of the tool 802, such as initiating the heating of a heating element, stopping the heating of a heating element, rotating a heating element, acquiring temperature measurements from temperature sensors, and so on. The wireline 812 may be raised and lowered within the well 804 to various depths using devices known in the art, such as a reel and drum apparatus in a service truck having the various components of a wireline system. The monitoring and control system 814 may facilitate operation of the wireline tool 802 in the wellbore 806 and may receive data from tool 802 to produce temperature data 816 (for example, temperature measurements). The monitoring and control system 814 may include one or more computer systems or devices. The monitoring and control system 812 may store the temperature data 816 and, in some embodiments, may have the capability of analyzing the temperature data 816 in accordance with techniques described in the disclosure. In some embodiments, as shown in FIG. 8, the temperature data 816 may be communicated to another system (for example, the thermal response processing system 804) for analysis.

Although the embodiment shown in FIG. 8 depicts a wireline tool, in other embodiments, the downhole thermal response tool 802 may be adapted for use as other suitable tools for insertion in to the wellbore 806. In other embodiments, the downhole thermal response tool 802 may be deployed in other manners, such as by a slickline, coiled tubing, or a pipe string. For example, in some embodiments, the downhole thermal response tool 802 or its functionality can be incorporated into a measurement-while-drilling (MWD) apparatus or logging-while-drilling LWD apparatus (such as in a bottomhole assembly). An MWD or LWD apparatus may have components or functionality in common with wireline tools (for example, transmitting and receiving antennas, sensors, etc.), but may be designed and constructed to endure and operate during drilling.

As described in the disclosure, embodiments of the thermal response tool 802 may temperature sensors and heating elements to enable the measurement of temperatures of downhole fluids and the subsequent determination of the thermal response (for example, the heating and cooling rates) of the fluids. As described in the disclosure, the temperature measurements may be used by the thermal response processing system 804 to determine a reference bulk volume of oil, a calculated bulk volume of oil, and a free water level, as described in the disclosure.

In some embodiments, the thermal response processing system 804 may be used to determine the fluid properties of a downhole fluid based on a thermal response determined from temperature measurements acquired by the downhole thermal response tool 802. The fluid properties may then be used to further plan and perform exploration, management, and assessment of the reservoir.

FIG. 8 also depicts components of the thermal response processing system in accordance with an embodiment of the disclosure. As shown in FIG. 8, the thermal response processing system may include a processor 820, a memory 822, and a display 824. It should be appreciated that the thermal response processing system may include other components that are omitted for clarity, such as a network interface, input device, etc.

The processor 820 (as used the disclosure, the term "processor" encompasses microprocessors) may include one or more processors having the capability to receive and process well log data, such as data generating from a wireline tool or from a logging while drilling tool. In some embodiments, the processor 820 may include an application-specific integrated circuit (AISC). In some embodiments, the processor 820 may include a reduced instruction set (RISC) processor. Additionally, the processor 820 may include a single-core processors and multicore processors and may include graphics processors. Multiple processors may be employed to provide for parallel or sequential execution of one or more of the techniques described in the disclosure. The processor 820 may receive instructions and data from a memory (for example, memory 822).

The memory 822 (which may include one or more tangible non-transitory computer readable storage mediums) may include volatile memory, such as random access memory (RAM), and non-volatile memory, such as ROM, flash memory, a hard drive, any other suitable optical, magnetic, or solid-state storage medium, or a combination thereof. The memory 822 may be accessible by the processor 820. The memory 822 may store executable computer code. The executable computer code may include computer program instructions for implementing one or more techniques described in the disclosure. For example, the executable computer code may include thermal response determination instructions 826 to implement one or more embodiments of the present disclosure. In some embodiments, the thermal response determination instructions 826 may receive, as input, temperature data 816 and provide, as output, a thermal response of a downhole fluid associated with the temperature data 816. The outputs may be stored in the memory 822.

Additionally, the memory 822 the executable computer code may include fluid properties determination instructions 828 and a fluids database 630 to implement one or more embodiments of the present disclosure. The fluid properties determination instructions 828 may receive, as input, a thermal response of a downhole fluid determined by the thermal response determination instructions 828. As described in disclosure, the thermal response of the downhole fluid may be compared to thermal responses of known fluids. For example, the fluids databases 630 may include known fluids and associated thermal responses and fluid properties. As described supra, by comparing the thermal response of the downhole fluid to the thermal responses of known fluids from the database 828, fluid properties of the downhole fluid may be determined.

The display 824 may include a cathode ray tube (CRT) display, liquid crystal display (LCD), an organic light emitting diode (OLED) display, or other suitable display. The display 824 may display a user interface (for example, a graphical user interface). In accordance with some embodiments, the display 824 may be a touch screen and may include or be provided with touch sensitive elements through which a user may interact with the user interface. In some embodiments, the display 824 may display the thermal response, fluid properties, or both of a downhole fluid measured by the downhole thermal response tool 802 in accordance with the techniques described in the disclosure.

In some embodiments, the thermal response processing system 804 may include a network interface (not shown) that may provide for communication between the thermal response processing system and other devices. The network interface may include a wired network interface. The network interface may communicate with networks, such as the Internet, an intranet, a wide area network (WAN), a local area network (LAN), a metropolitan area network (MAN) or other networks. Communication over networks may use suitable standards, protocols, and technologies, such as Ethernet Bluetooth, Wireless Fidelity (Wi-Fi) (e.g., IEEE 802.11 standards), and other standards, protocols, and technologies.

In some embodiments, the thermal response processing system 804 may be coupled to an input device (for example, one or more input devices). The input devices may include, for example, a keyboard, a mouse, a microphone, or other input devices. In some embodiments, the input device may enable interaction with a user interface displayed on the display 824. For example, in some embodiments, the input devices may enable the entry of inputs to a process for determining free water level and parameters used in the process (for example, parameters of a selected water saturation model used in the determination of the calculated bulk volume of oil discussed in the disclosure).

The downhole thermal response tool and associated fluid properties determination described supra improve the accuracy of the determination of downhole fluids and provides a more direct measurement of such fluid properties. The more accurate fluid properties may improve the drilling of wells to access hydrocarbon reservoirs in formations and may increase hydrocarbon production from a hydrocarbon reservoir. Moreover, the downhole thermal response tool may also provide for faster and less costly determinations of downhole fluid properties as compared to existing techniques that may require fluid sampling and fluid separation prior to analysis. Moreover, the fluid properties determination described supra may be more computationally efficient than previous techniques, For example, as compared to previous techniques, the fluid properties determination may reduce the computation cost and time required to determine the fluid properties of downhole fluids in a formation having a hydrocarbon reservoir.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A method of determining the properties of a fluid, comprising:
    inserting a tool into a wellbore, the tool comprising:
        a tool body; and
        a plurality of temperature sensors disposed at a respective plurality of positions along an axial length of the tool body, each of the plurality of temperature sensors configured to acquire a temperature measurement of the fluid external to the tool body, wherein the each of the plurality of temperature sensors comprises a circular temperature sensor disposed around an outer circumference of the tool body;
    a heating element disposed at a position along the axial length of the tool body such that the heating element is disposed between two of the plurality of temperature sensors, the heating element configured to heat a region external to the tool body, wherein the heating element comprises a radiofrequency (RF) source coupled to a directional RF antenna and the RF source comprises a rotational RF source rotatable around a circumference of the tool body;
    receiving a respective plurality of temperature measurements from the plurality of temperature sensors of the tool;
    determining a thermal response of the fluid based on the plurality of temperature measurements; and
    determining a viscosity of the fluid using the thermal response, the viscosity determined from the thermal response of a heating time at a first temperature of the plurality of temperature measurements and a cooling time at a second temperature of the plurality of temperature measurements;

determining a composition of the fluid using the viscosity and at least one temperature of the plurality of temperature measurements, wherein determining a composition of the fluid using the viscosity and at least one temperature of the plurality of temperature measurements comprises:

matching the viscosity of the fluid at the at least one temperature to the viscosity of a known fluid; and determining a composition of the fluid from the composition of the known fluid.

2. The method of claim 1, comprising determining at least one property of the fluid using the thermal response, wherein determining at least one property of the fluid using the thermal response comprises:

matching the thermal response of the fluid to a thermal response of a known fluid; and determining a property of the fluid from a property of the known fluid.

3. The method of claim 2, wherein the at least one property includes at least one of a heat capacity, a diffusivity, and a thermal conductivity.

4. The method of claim 1, wherein determining the thermal response of the fluid based on the plurality of temperature measurements comprises plotting the plurality of temperature measurements versus time.

5. The method of claim 1, wherein each of the plurality of temperature sensors comprises a thermocouple.

6. The method of claim 1, wherein the heating element comprises a first heating element, the position comprises a first position, and the region comprises a first region, the tool comprising a second heating element disposed at a second position along the axial length of the tool body such that the heating element is disposed between a different two of the plurality of temperature sensors, the second heating element configured to heat the fluid.

7. A system for determining the properties of a fluid in a wellbore, the system comprising:

a processor;

a non-transitory computer-readable memory accessible by the processor, the memory having executable code stored thereon, the executable code comprising a set of instructions that causes the processor to perform operations that include:

receiving a respective plurality of temperature measurements from a plurality of temperature sensors of a tool inserted in the wellbore, the tool comprising:

a tool body; and the plurality of temperature sensors disposed at a respective plurality of positions along an axial length of the tool body, each of the plurality of temperature sensors configured to acquire the respective plurality of temperature measurements of the fluid external to the tool body, wherein the each of the plurality of temperature sensors comprises a circular temperature sensor disposed around an outer circumference of the tool body;

a heating element disposed at a position along the axial length of the tool body such that the heating element is disposed between two of the plurality of temperature sensors, the heating element configured to heat a region external to the tool body, wherein the heating element comprises a radiofrequency (RF) source coupled to a directional RF antenna and the RF source comprises a rotational RF source rotatable around a circumference of the tool body;

determining a thermal response of the fluid based on the plurality of temperature measurements; and determining a viscosity of the fluid using the thermal response, the viscosity determined from the thermal response of a heating time at a first temperature of the plurality of temperature measurements and a cooling time at a second temperature of the plurality of temperature measurements; and determining a composition of the fluid using the viscosity and at least one temperature of the plurality of temperature measurements, wherein determining a composition of the fluid using the viscosity and at least one temperature of the plurality of temperature measurements comprises:

matching the viscosity of the fluid at the at least one temperature to the viscosity of a known fluid; and determining a composition of the fluid from the composition of the known fluid.

8. The system of claim 7, the operations comprising determining at least one property of the fluid using the thermal response, wherein determining at least one property of the fluid using the thermal response comprises:

matching the thermal response of the fluid to a thermal response of a known fluid; and determining a property of the fluid from a property of the known fluid.

9. The system of claim 8, wherein the at least one property includes at least one of a heat capacity, a diffusivity, and a thermal conductivity.

10. The system of claim 7, wherein determining the thermal response of the fluid based on the plurality of temperature measurements comprises plotting the plurality of temperature measurements versus time.

* * * * *